(12) United States Patent
Ribolzi et al.

(10) Patent No.: US 8,641,657 B2
(45) Date of Patent: Feb. 4, 2014

(54) BLOOD TRANSFER CHAMBER

(75) Inventors: Francesco Ribolzi, Varese (IT); Ranko Sakota, Giugliano (IT); Luca Caleffi, Carpi (IT); Giuseppe Franzoni, Sassuolo (IT)

(73) Assignee: Gambro Lundia AB, Lund (SE)

( * ) Notice: Subject to any disclaimer, the term of this patent is extended or adjusted under 35 U.S.C. 154(b) by 367 days.

(21) Appl. No.: 12/517,020

(22) PCT Filed: Dec. 1, 2006

(86) PCT No.: PCT/IB2006/003439
§ 371 (c)(1),
(2), (4) Date: Jun. 16, 2010

(87) PCT Pub. No.: WO2008/065472
PCT Pub. Date: Jun. 5, 2008

(65) Prior Publication Data
US 2010/0256547 A1     Oct. 7, 2010

(51) Int. Cl.
*A61M 5/00* (2006.01)
*A61M 37/00* (2006.01)
*B01D 29/00* (2006.01)

(52) U.S. Cl.
USPC .......................... 604/7; 604/6.09; 210/497.1

(58) Field of Classification Search
USPC .................. 604/7, 6.09; 210/497.1
See application file for complete search history.

(56) References Cited

U.S. PATENT DOCUMENTS

| | | | |
|---|---|---|---|
| 4,052,315 A | 10/1977 | Lindsay, Jr. et al. | |
| 4,666,598 A * | 5/1987 | Heath et al. | 210/239 |
| 4,770,787 A * | 9/1988 | Heath et al. | 210/646 |
| 5,328,461 A | 7/1994 | Utterberg | |
| 5,330,425 A | 7/1994 | Utterberg | |
| 5,489,385 A * | 2/1996 | Raabe et al. | 210/448 |
| 5,503,801 A | 4/1996 | Brugger | |
| 5,545,318 A * | 8/1996 | Richmond | 210/232 |
| 5,591,251 A * | 1/1997 | Brugger | 95/242 |
| 5,674,199 A | 10/1997 | Brugger | |
| 5,895,578 A * | 4/1999 | Simard et al. | 210/636 |
| 5,941,842 A * | 8/1999 | Steele et al. | 604/4.01 |
| 6,187,198 B1 * | 2/2001 | Utterberg | 210/645 |
| 6,464,878 B2 * | 10/2002 | Utterberg | 210/645 |
| 6,468,427 B1 | 10/2002 | Frey | |
| 6,949,214 B2 * | 9/2005 | Frey | 264/328.1 |
| 2003/0006187 A1 | 1/2003 | Frey | |
| 2003/0138348 A1 * | 7/2003 | Bell et al. | 422/44 |
| 2004/0186416 A1 * | 9/2004 | Caleffi | 604/6.16 |
| 2004/0219059 A1 * | 11/2004 | Barringer et al. | 422/44 |
| 2005/0063860 A1 * | 3/2005 | Carpenter et al. | 422/45 |
| 2010/0274171 A1 * | 10/2010 | Caleffi et al. | 604/6.09 |

FOREIGN PATENT DOCUMENTS

| | | |
|---|---|---|
| CH | 637 020 A5 | 7/1983 |
| DE | 32 02 582 A1 | 9/1982 |
| DE | 31 43 456 A1 | 5/1983 |
| EP | 0 161 803 A2 | 11/1985 |
| EP | 0 174 420 A2 | 3/1986 |
| EP | 0 248 938 A1 | 12/1987 |
| EP | 0 568 265 A2 | 11/1993 |
| GB | 2 028 976 A | 3/1980 |
| JP | 7299136 A | 11/1995 |
| JP | 8257114 A | 10/1996 |
| JP | 11290454 A | 10/1999 |
| JP | 3066867 U | 12/1999 |
| JP | 2003/265601 A | 9/2003 |
| WO | 81/01793 A1 | 7/1981 |
| WO | 95/21644 A1 | 8/1995 |
| WO | 00/18482 A1 | 4/2000 |
| WO | 01/07136 A1 | 2/2001 |

* cited by examiner

*Primary Examiner* — Leslie Deak
*Assistant Examiner* — Guy K Townsend
(74) *Attorney, Agent, or Firm* — Pearne & Gordon LLP

(57) ABSTRACT

In a blood transfer chamber, a filter (4) is arranged at an outlet located on a bottom of the chamber. The filter is truncoconical with a vertically-disposed axis. The filter has a plurality of openings (13, 14) for fluid passage, a size of which openings increases gradually in an upwards direction going from bottom to top of the chamber. The filter is used in a venous air-blood separation chamber of a dialysis set. The invention enables a reduction of a risk of hemolysis during treatment as well as a reduction of the risk of formation of air bubble retention in the filter during a priming stage.

38 Claims, 10 Drawing Sheets

BLOOD TRANSFER CHAMBER

BACKGROUND OF THE INVENTION

The invention relates to a blood transfer chamber.

Specifically, though not exclusively, the invention can be usefully applied in an extracorporeal circuit for performing an extracorporeal blood treatment, such as for example a dialysis treatment.

U.S. Pat. No. 5,503,801 teaches a bubble trap provided at a bottom thereof with a seating for housing a hollow truncoconical filter. On a lateral wall thereof, the filter exhibits openings which enable passage of blood while trapping larger particulate material of a certain size, such as blood clots and extraneous materials. Each opening substantially defines the same blood passage section.

U.S. Pat. No. 5,328,461 teaches a blow moulded venous drip chamber for hemodialysis in which a tubular blood filter is inserted, made of a plastic material. All the filter openings substantially exhibit the same passage section size.

Other examples of filters for a medical drip chamber are described in DE 3202582, GB 2028976, WO 81/01793, JP 2003/265601, JP 11290454, JP 8257114, DE 3143456, and JP 7299136. In these examples the lateral wall of the filter exhibits openings distributed essentially uniformly.

One of the drawbacks in the prior art is that the blood passage through the filter can cause hemolysis.

A further drawback in the prior art is the risk of stagnation of air bubbles in the upper part of the filter during the extracorporeal blood circuit priming stage. The priming stage, as is known, precedes the actual treatment. During the treatment the blood passes through the filter from the outside towards the inside, while normally during the priming stage a priming fluid (normally an isotonic saline solution) passes from the inside to the outside of the filter. During this priming stage any air bubbles contained in the priming fluid can be trapped internally of the filter, with the probability that they will then be sent on, during treatment, towards the outlet of the blood chamber, with the consequence that the air bubble sensor is activated, causing an alarm to be set off and hence blocking the treatment.

SUMMARY OF THE INVENTION

An aim of the present invention is to provide a blood chamber having a filter which is able to obviate the above-mentioned drawbacks in the prior art.

A further aim of the invention is to provide a constructionally simple and economical filter.

An advantage of the invention is to provide a blood chamber which is provided with a filter that produces a relatively small-scale hemolysis effect.

A further advantage of the invention is that it makes available a blood chamber provided with a filter which exhibits a low risk of trapping air bubbles, including in the priming stage.

These aims and others besides are all attained by the invention as it is characterised in one or more of the appended claims.

Further characteristics and advantages of the present invention will better emerge from the detailed description that follows of at least a preferred embodiment thereof, illustrated by way of non-limiting example in the accompanying figures of the drawings.

BRIEF DESCRIPTION OF THE DRAWINGS

The description will now follow, with reference to the accompanying figures of the drawings, which are provided purely by way of non-limiting example, and in which.

DETAILED DESCRIPTION

Figure 1:
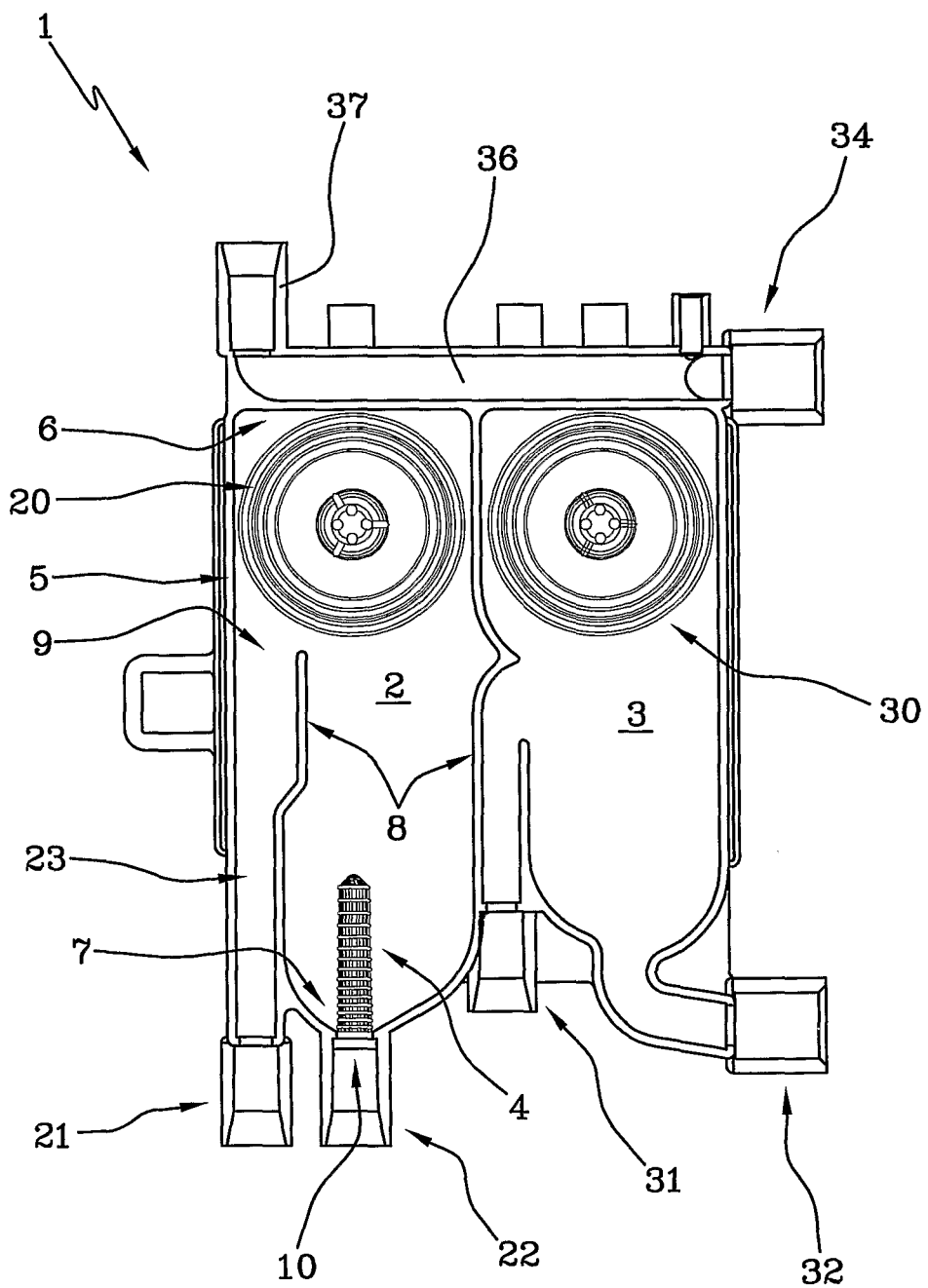
FIG. 1 is a cartridge, or cassette, comprising two separate blood chambers, in one of which a filter according to the invention is arranged.
Figure 2:
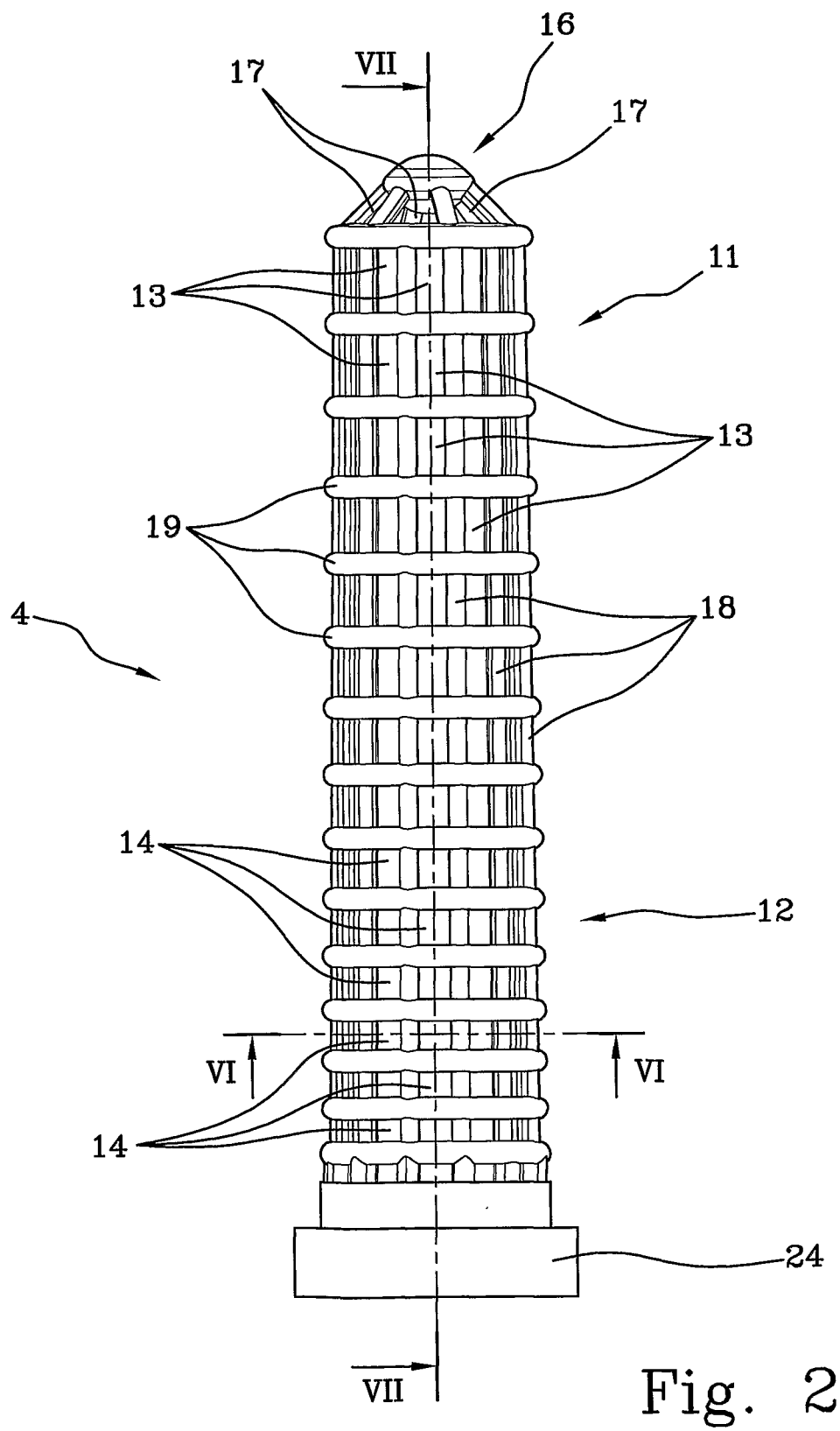
FIG. 2 is a side view of the filter inserted in the cartridge of FIG. 1.
Figure 3:
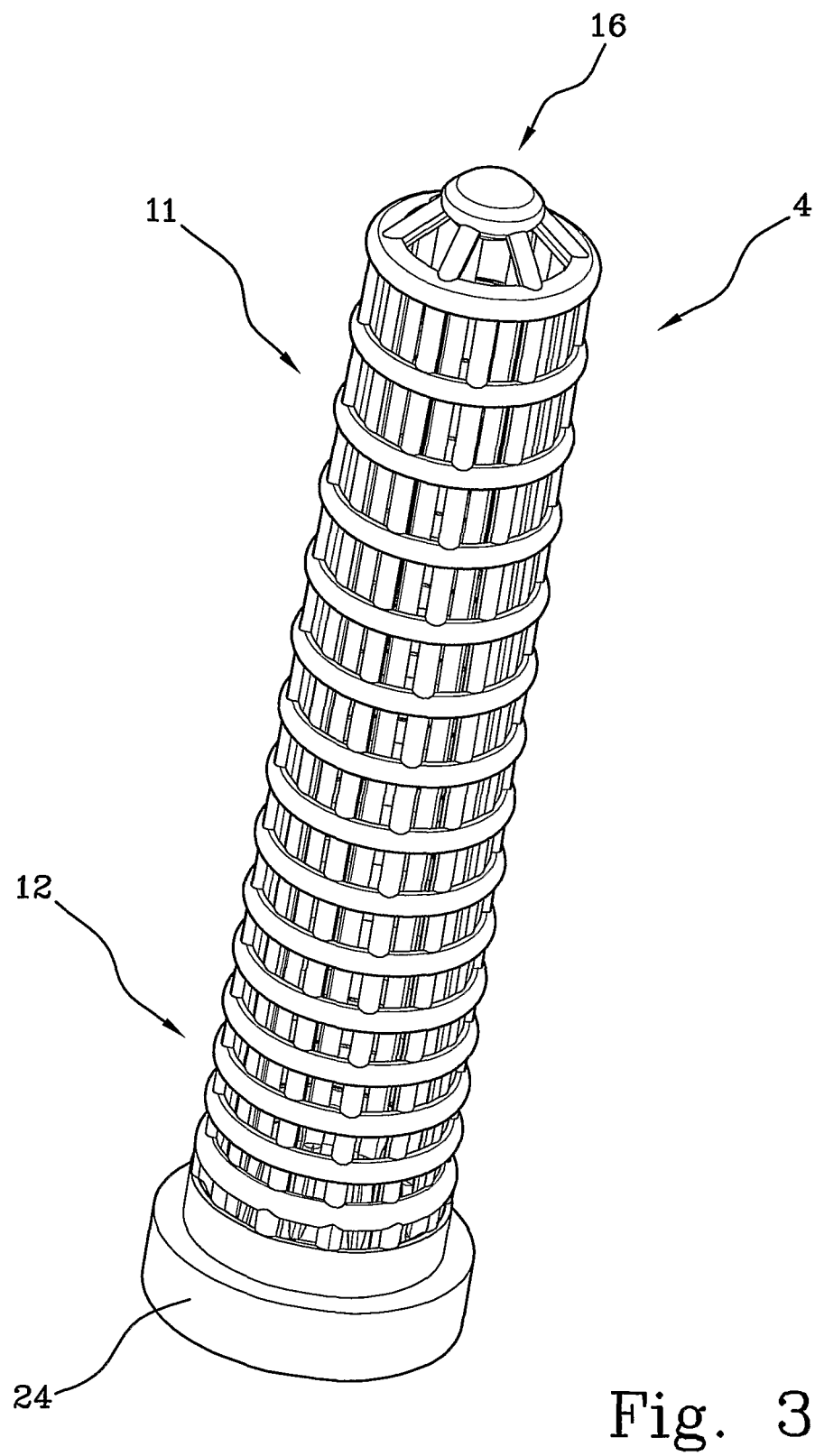
FIG. 3 is a perspective view of the filter of FIG. 2.
Figure 4:
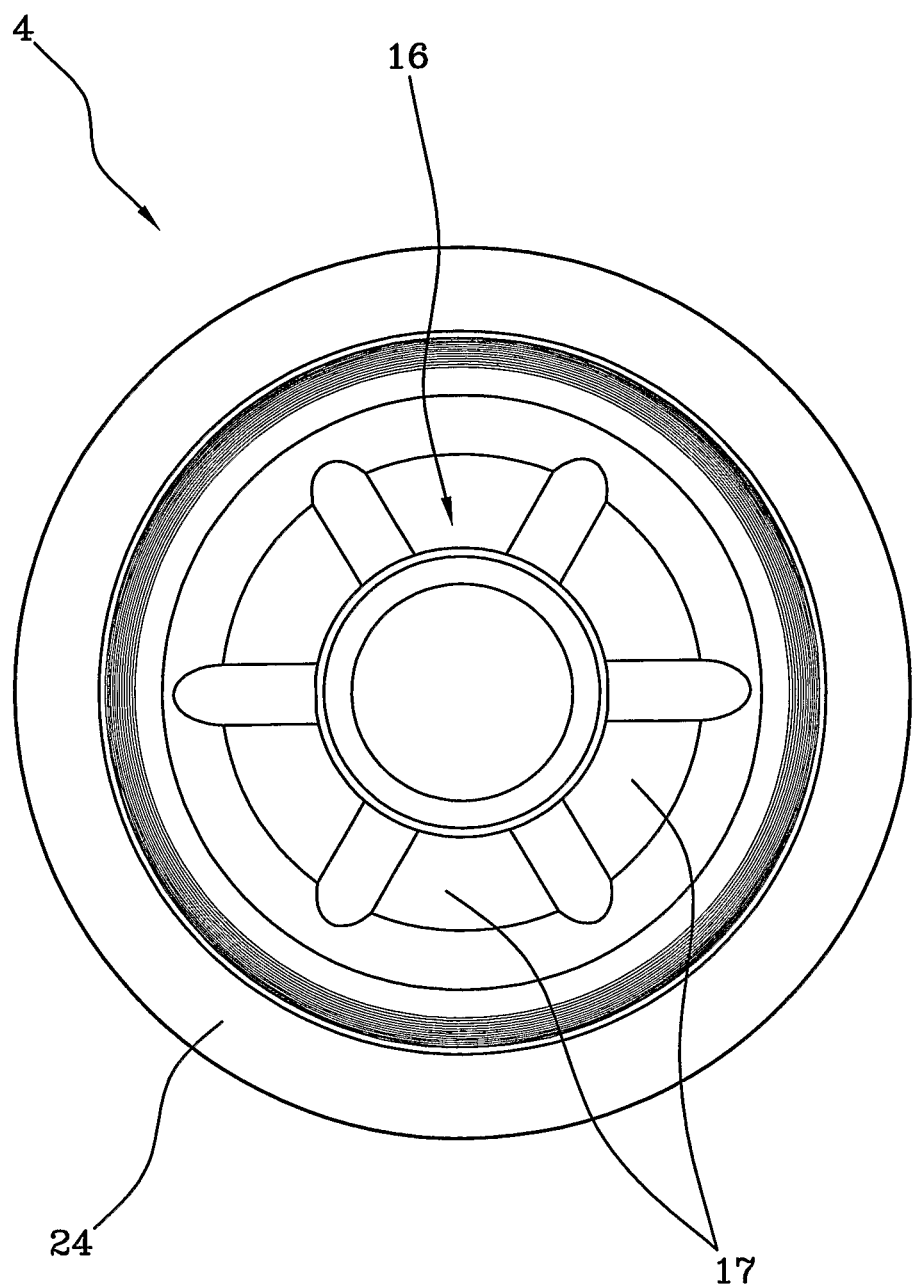
FIG. 4 is an enlarged view from above of FIG. 2.
Figure 5:
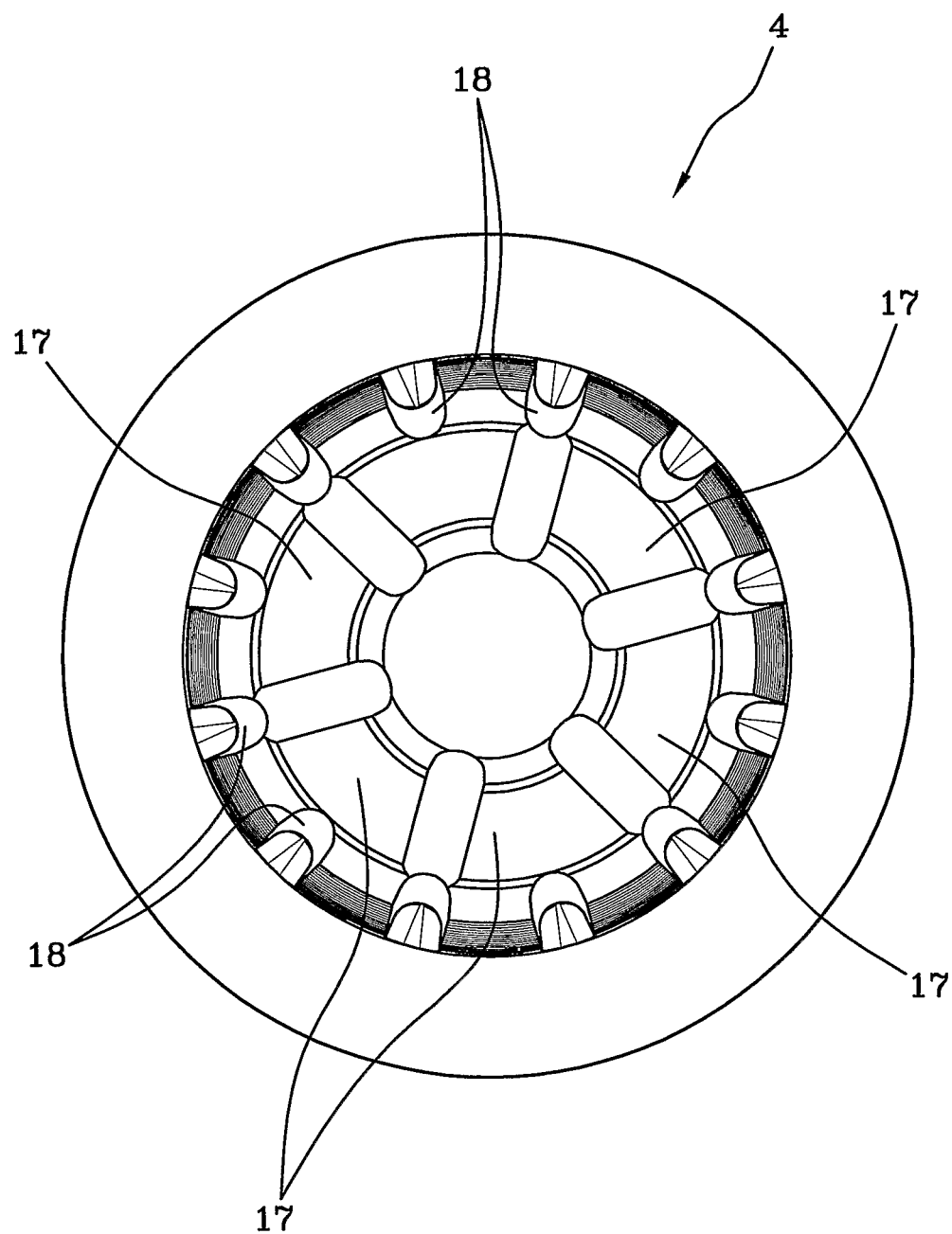
FIG. 5 is an enlarged view from below of FIG. 2.
Figure 6:
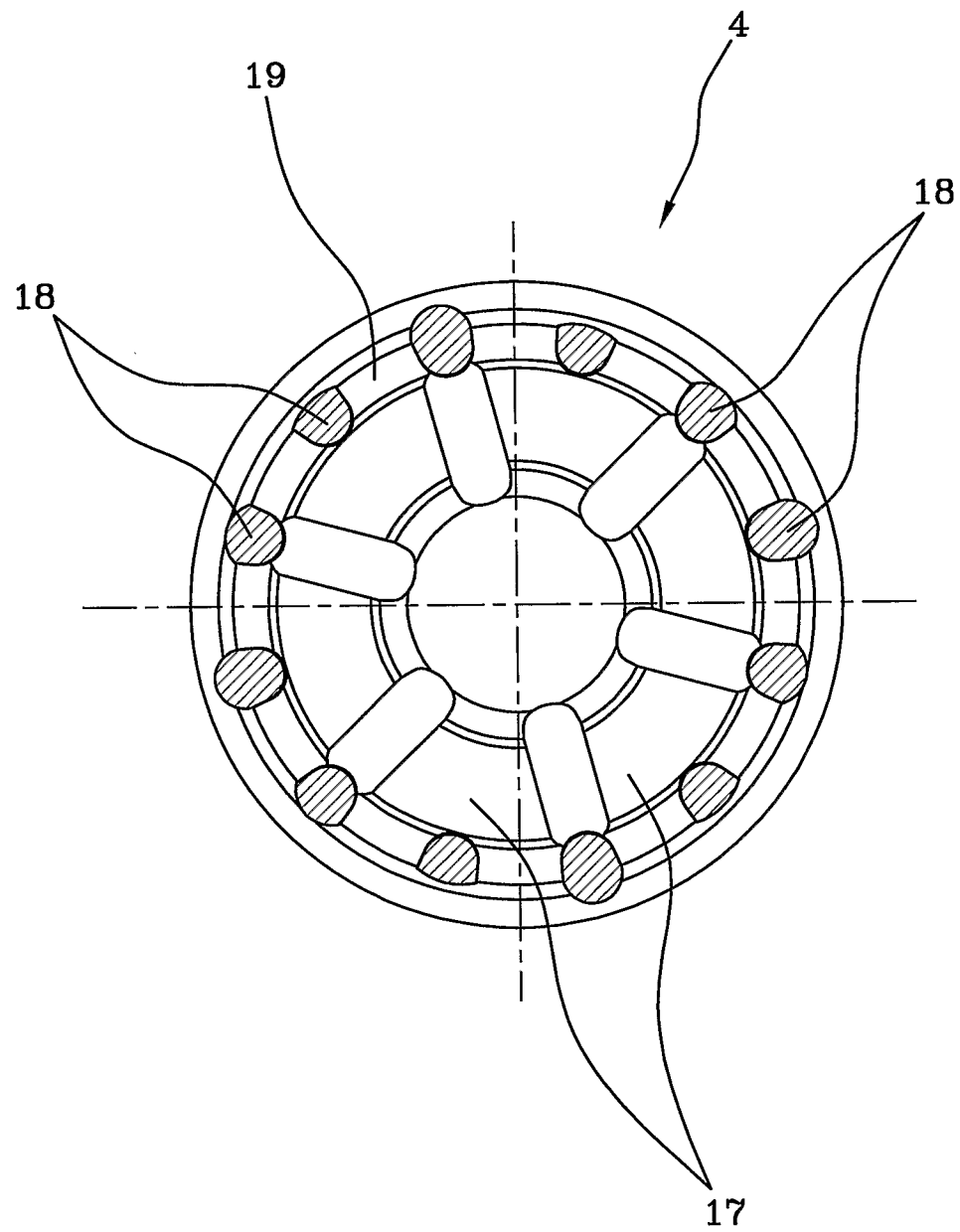
FIG. 6 is an enlarged section according to line VI-VI of FIG. 2.
Figure 7:
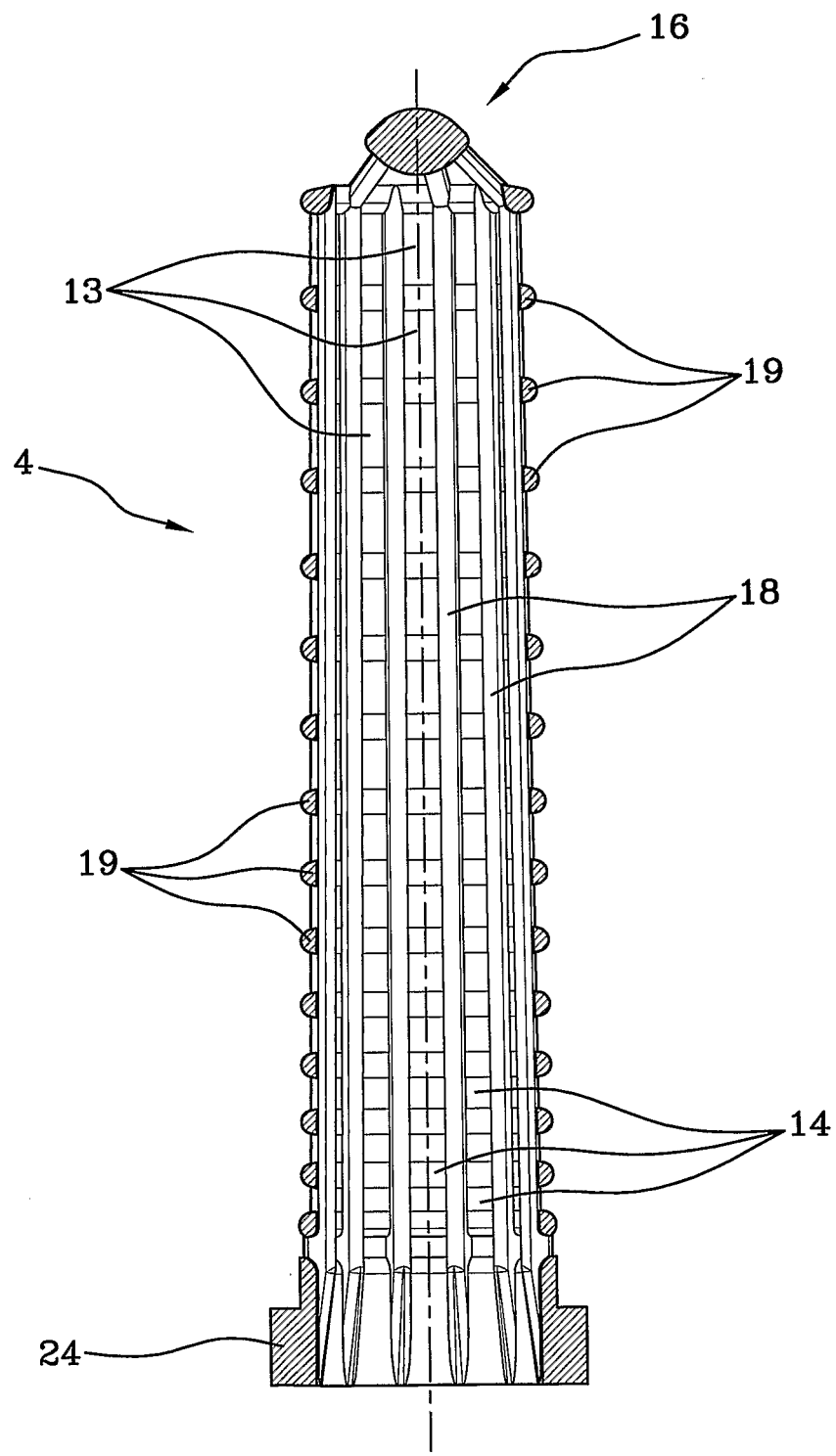
FIG. 7 is an enlarged section according to line VII-VII of FIG. 2.

With reference to FIG. 1, number 1 denotes in its entirety a cartridge, or cassette, for a dialysis set. The cartridge 1 is an element made of a plastic material, for example by injection moulding. The cartridge 1 is rigid and transparent. The cartridge 1 defines a venous blood chamber 2 and an arterial blood chamber 3. The two blood chambers 2 and 3 are integral with the cartridge. Each blood chamber 2 and 3 defines a gas-liquid (air-blood) separation chamber. Each blood chamber 2 and 3 is flat-shaped, with one dimension considerably smaller than the other two dimensions. The two blood chambers 2 and 3 are arranged side-by-side on a same lie plane. Each blood chamber 2 and 3 is provided with a membrane device 20 and 30 of known type, configured for coupling with a pressure meter of a dialysis monitor. Each blood chamber 2 and 3 is configured to give rise during use to a liquid level, above which a gas is present. The venous blood chamber 2 is provided with a filter 4 configured for trapping particles of predetermined size contained in the blood, such as for example blood clots or other particles which must not reach the patient's vascular access. In the following description reference will be made to the filter 4 inserted in the venous blood chamber 2 of the cartridge 1. However the present invention can also be applied to a filter for the treatment of particles inserted in any blood transfer chamber arranged in an extracorporeal blood circuit, in which the chamber is provided with an inlet and an outlet for defining a blood transfer flow in the chamber, and in which the filter works internally of the chamber between the inlet and the outlet.

The venous chamber comprises a recipient 5 having a top 6, a bottom 7, a lateral wall 8, an inlet 9 and an outlet 10. The lateral wall 8 extends between the top 6 and the bottom 7. The lateral wall 8 has at least a first transversal section having a first area. The outlet 10 is arranged on the bottom 7. The outlet has a second transversal section having a second area which is smaller than the first area. The recipient 5 is therefore wider than the outlet 10. The filter 4 is arranged between the inlet 9 and the outlet 10. The filter extends between the bottom 7 and the top 6. The filter 4 has a lower end which is solidly fixed to the bottom about the outlet 10. In the illustrated embodiment the second transversal section (of the outlet 10) is circular. In the illustrated example, and going from top to bottom, the lateral wall 8 exhibits a variable transversal section. In particular the transversal section of greater area is arranged at the top. In the lower part of the chamber 2, in particular at the bottom 7 thereof, the transversal section of the lateral wall gradually reduces up until it reaches the outlet 10.

The venous chamber 2 has two access ports 21 and 22, arranged inferiorly therein. Each access port 21 and 22 is formed by a tubular connection configured for coupling with a blood transport pipe. A first access port 21 communicates with the blood inlet 9 of the venous chamber 2. A conduit 23 integrated in the cartridge connects the first access port 21 with the blood inlet 9. The conduit 23 increases the passage section thereof going from the bottom towards the top. The upper inlet section 9 is larger than a lower initial section of the conduit 23. The conduit 23 extends vertically on a side of the chamber 2. A second access port 22 is in communication with the blood outlet 10 of the venous chamber. The blood inlet 9 is arranged at a higher level than the blood outlet 10, with reference to a use configuration of the cartridge (in vertical elevation, as in FIG. 1). In particular the inlet 9 is arranged closer to the top 6 of the chamber than to the bottom 7 thereof. In particular the inlet 9 is arranged closer to the top 6 of the chamber than to the outlet 10 located at the bottom 7 of the chamber. The inlet 9 is arranged higher than a top end of the filter 4. This arrangement between the inlet 9, the filter 4, the top 6 and the bottom 7 of the chamber generates, during use, a homogeneous and well-distributed blood flow with a reduced risk of hemolysis, while not sacrificing filter filtering efficiency.

In figures from 2 to 8 the filter 4 structure is illustrated in greater detail. The filter 4 has a filtering wall comprising an upper portion 11 and a lower portion 12. The upper portion 11 exhibits a plurality of upper openings 13. The lower portion 12 exhibits a plurality of lower openings 14. The upper openings 13 and the lower openings 14 are configured in such a way that the upper portion 11 offers a resistance to fluid passage per surface unit which is lower than that of the lower portion 12. The upper portion 11 has a first value, which is indicative of the resistance to fluid passage per surface unit (or passage section) and which is defined by the surface (or passage section) of the upper openings 13 per surface unit of the upper portion 11. The lower portion 12 has a second value defined by the surface of the lower openings 14 per surface unit of the lower portion 12. In the illustrated embodiment the first value is greater than the second value. The first value and the second value indicate, substantially, an empty-full ratio of the filtering surface in terms of openings and non-perforated surface area, defining the lateral filtering wall of the filter 4. This empty-full ratio can provide an indication of the resistance to fluid passage per unit of filtering surface. There are however other factors, apart from the empty-full ratio, which can provide an indication of the resistance to fluid passage per unit of filtering surface, such as for example the shape of the passage openings, the profile of the walls delimiting the passage openings, the width in absolute terms of the passage openings, the distribution, closer or more spaced, of the passage openings, and so on. The fact of generating a greater resistance to the fluid passage for the lower portion 12 with respect to the upper portion 11 (for example by realising smaller openings and/or less closely spaced openings in the lower portion 12) determines, as has been experimentally observed, a greater homogeneity of the blood flow rate crossing the filter in the various openings. Thus, with a same total blood flow, the velocity of the various blood particles is distributed more regularly (more or less constant for all the particles), so that the maximum velocity of the various blood particles (punctual, or local, velocity maximum) is reduced with a same total flow. This reduces the risk of hemolysis. Also, the presence of larger openings in the upper portion 11 reduces the risk of stagnation of air bubbles in the priming procedure, in which the flow goes from the inside towards the outside of the tubular filtering wall, i.e. in an inverse direction with respect to the extracorporeal blood treatment stage (for example dialysis). The presence of larger openings in the upper portion 11 reduces the risk of stagnation of air bubbles in the priming procedure also when the priming flow goes from the outside towards the inside of the tubular filtering wall, In the illustrated embodiment, the upper openings 13 are on average larger than the lower openings 14. In a further embodiment (not illustrated) the upper openings 13 are more closely distributed with respect to the lower openings 14.

The filter 4 is made of a single piece of a plastic material. The filter 4 is made by moulding, for example injection-moulding of plastic. The filtering wall of the filter 4 is tubular with an open lower end. In a further embodiment, not illustrated, the lower end of the filtering tubular wall is closed by a further filtering wall. The filtering wall is essentially trunco-conical (as in the illustrated embodiment, with a slight conicity in an upwards direction) or cylindrical. The filtering wall is taller than it is wide. In other words the filtering wall is oblong in a vertical direction. In particular the filtering wall is at least twice (or three times) as tall it is wide. In the illustrated embodiment the filtering wall is about four times as tall is it is wide (diameter) at the base. The upper openings 13 are all bigger than the lower openings 14. The size of the upper 13 and lower 14 openings increases proceeding along the filtering wall starting from the bottom and going in an upwards direction. This increase in size is gradual. Further, the height of the lower 14 and upper 13 openings also increases along the filtering wall going from the bottom towards the top. This increase is also gradual. In the illustrated embodiment the width of the lower 14 and upper 13 openings is substantially constant. In other preferred embodiments the width of the upper openings 13 and/or lower openings 14 increases proceeding along the filtering wall going from the bottom towards the top. This increase in width can be gradual.

Figure 8:
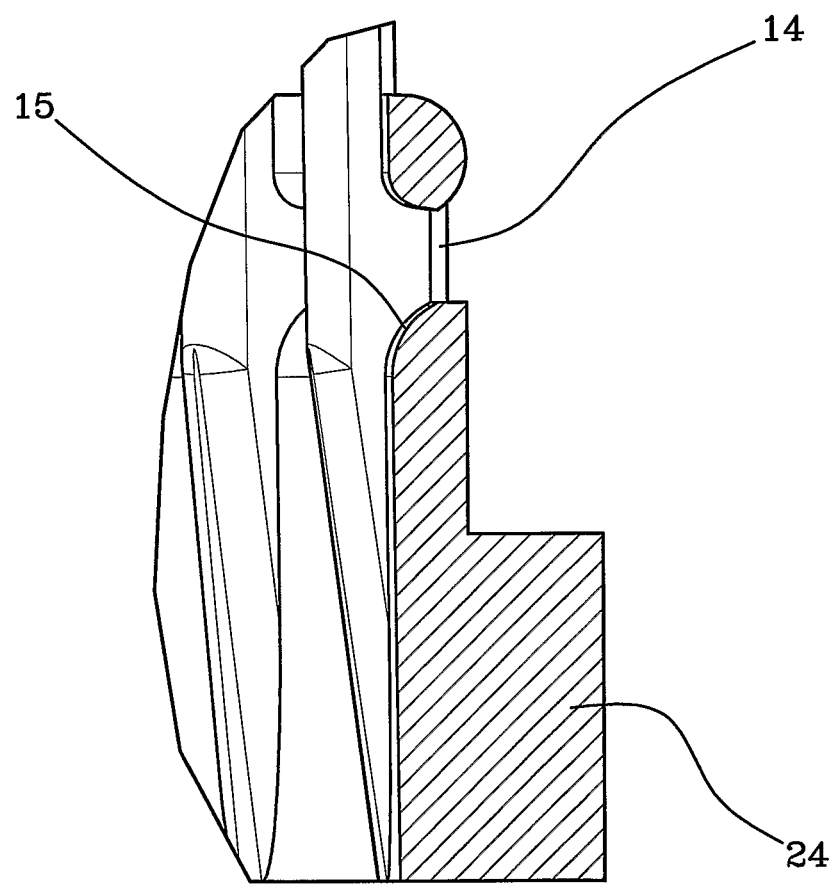
FIG. 8 is a detail of FIG. 7 in large-scale.

At least a part of the upper openings 13 is from one and a half to six times bigger than at least a part of the lower openings 14. The upper openings 13 located highest, or furthest from the outlet 10, are at least two (or three) times bigger than the lowest openings, or those closest to the outlet 10. In the illustrated embodiment the highest upper openings 13, i.e. furthest from the outlet 10, are about three and a half times bigger than the lower openings located lowest, or closest to the outlet 10. The upper 13 and lower 14 openings arranged at a same distance from the outlet 10 are the same size. Some openings, upper 13 and lower 14, which are on average furthest from the outlet 10, are bigger with respect to other openings arranged on average closer to the outlet 10. To summarise, the size of the openings 13 and 14 grows gradually as they distance from the outlet 10 so that, as previously mentioned, the resistance to fluid passage offered by the lower portion of the filtering wall is greater with respect to the resistance to fluid passage offered by the upper portion. In particular the lower openings which are arranged lowest of all (which are effectively those of the last lower row, closest to the outlet 10) are smaller with respect to all the other openings both lower 14 and upper 13. The smallest lower openings 14 (those closest to the outlet 10) are arranged in an annular fashion about a longitudinal axis of the filtering wall. Each of the smallest lower openings 14 (illustrated in detail in FIG. 8) is inferiorly delimited by an inclined surface 15, in which the inclination extends downwards towards the bottom, proceeding from the outside towards the inside of the tubular filtering wall. The inclined surface 15 is a connecting surface. The inclined surface 15 is curved towards the outside (convex). This inclination reduces the risk of hemolysis, which is an especially great risk at the openings closest to the outlet 10.

In other embodiments (not illustrated) all or at least the majority of to the other lower and/or upper openings are each inferiorly delimited by an inclined surface (similar to the inclined surface 15), in which the inclination extends downwards going from the inside towards the outside of the tubular filtering wall.

The filtering wall is superiorly provided with a head 16 which is closed or which, as in the illustrated example, exhibits a further plurality of openings 17 for fluid passage. The filtering wall comprises a plurality of first ribs 18 and a plurality of second ribs 19. The first ribs 18 extend axially. The second ribs 19 extend circumferentially. The first ribs 18 intersect the second ribs 19. The first ribs 18 are reciprocally aligned and distanced in a circumferential direction. Each first rib 18 is located at a same circumferential distance from the two first ribs 18 adjacent thereto. The second ribs 19 are reciprocally coaxial and distanced reciprocally in an axial direction. Each second rib 19 is more distant in the axial direction from the immediately-above second rib 19 than from the immediately-below second rib 19. The second ribs 19 are arranged more externally with respect to the first ribs 18 in order to enable the filter to be more easily manufactured by injection moulding. The first ribs 18 have a rounded section towards the outside of the filtering wall. The second ribs 19 have a rounded section towards the outside of the filtering wall.

The upper openings 13 arranged in the upper half of the filtering wall constitute a passage section per surface unit of the filtering wall which is comprised between 0.25 and 0.65. In particular the upper openings 13 arranged in the upper half of the filtering wall define a passage section per surface unit of the filtering wall of 0.45. The lower openings 14 in the lower half of the filtering wall constitute a passage section per surface unit of the filtering wall comprised between 0.15 and 0.55. In particular the lower openings 14 arranged in the lower half of the filtering wall define a passage section per surface unit of the filtering wall of 0.35.

As previously mentioned, the filtering wall is essentially truncoconical (or cylindrical). The upper 13 and lower 14 openings extend in a parallel direction to the generatrix of the filtering wall. The various lower 14 and upper 13 openings are arranged in an annular fashion about a longitudinal axis of the filtering wall. In a preferred embodiment, not illustrated, in place of a plurality of axially-distanced circumferential second ribs 19 a spiral rib is provided which develops from the bottom towards the top with a gradually increasing step, intersecting with the plurality of parallel longitudinal ribs. Two or more spiral ribs can be predisposed. The variation of the step enables a gradual variation in the resistance to fluid passage, generating openings with an average size that grows in the upper portion 11 of the filter and with an average size that decreases in the lower portion 12, in order to achieve a higher fluid resistance in the lower portion.

The lower 14 and upper 13 openings define overall a total passage section which is greater than the second area transversal section, i.e. the outlet section 10. In particular the total passage section is from five to ten times greater than the second area transversal section. In the specific case the total passage section is about seven and a half times greater than the second area transversal section.

The largest upper opening 13 (i.e. one of the openings located in the highest annular row) has a passage section having an area which is from a twentieth to a fiftieth as large as the second area transversal section. In the specific case the largest upper opening 13 has a passage section which is about a thirty-fifth as large as the second area transversal section.

The filter 4 has an annular base 24 configured for coupling with an annular seating afforded about the outlet 10 of the venous chamber 2.

Looking once more at FIG. 1, the arterial chamber 3 has two access ports 31 and 32 which are inferiorly arranged. Each access port 31 and 32 is formed by a tubular connection configured for coupling with a blood transport tube. A first access port 31 communicates with a blood inlet of the arterial chamber. A conduit integrated into the cartridge connects the first access port with the blood inlet. A second access port 32 communicates with a blood outlet of the arterial chamber. A conduit integrated into the cartridge connects the second access port 32 with the blood outlet. The blood inlet is arranged at a higher position than the blood outlet, with reference to a use configuration of the cartridge. The second access port 32 comprises a first tubular extension configured for coupling with a first end of a pump tube 33 (see FIG. 9). The cartridge 1 is provided with a second tubular extension 34 configured for coupling with a second end of the pump tube 33. The pump tube 33 is designed for coupling with a blood pump 35 (see FIG. 10). The pump tube 33 is open-ring configured. The blood pump 35 comprises, in the illustrated embodiment, a tube-deforming rotary pump (a peristaltic pump). The cartridge 1 integrates an internal conduit 36 which sets the second tubular extension 34 in communication with a tubular connector 37 designed for coupling with an end of a tract 38 of arterial line which leads to an inlet of the blood chamber of a blood treatment device 39, or membrane separator, in the case a dialyser.

Figure 9:
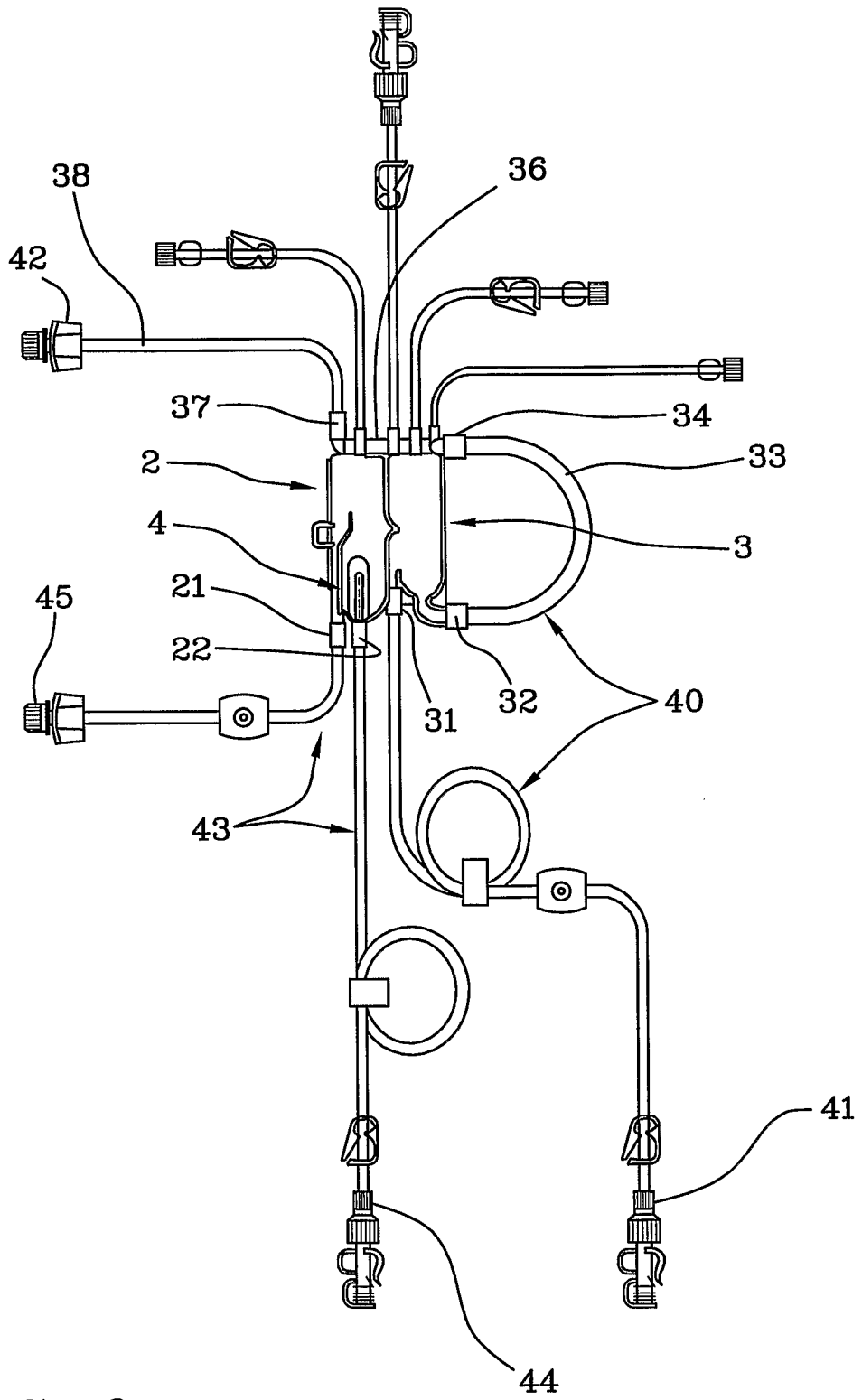
FIG. 9 is a dialysis set comprising the cartridge of FIG. 1.

FIG. 9 illustrates a dialysis set for blood transport in a dialysis treatment. The dialysis set comprises an arterial line 40 having a patient end 41 which is configured for coupling with a vascular access device (of known type and not illustrated), and a device end 42 configured for coupling with the inlet of the blood chamber of the blood treatment device 39. The dialysis set further comprises a venous line 43 having a patient end 44 which is configured for coupling with a vascular access device (of known type and not illustrated) and a device end 45 configured for coupling with the outlet of the blood chamber of the blood treatment device 39. The various and further elements of the dialysis set of FIG. 9 (service lines, anticoagulant line, access sites, clamps etc) are of known type and therefore not described in detail herein. The dialysis set can comprise the elements of any one of the dialysis sets of known type.

Figure 10:
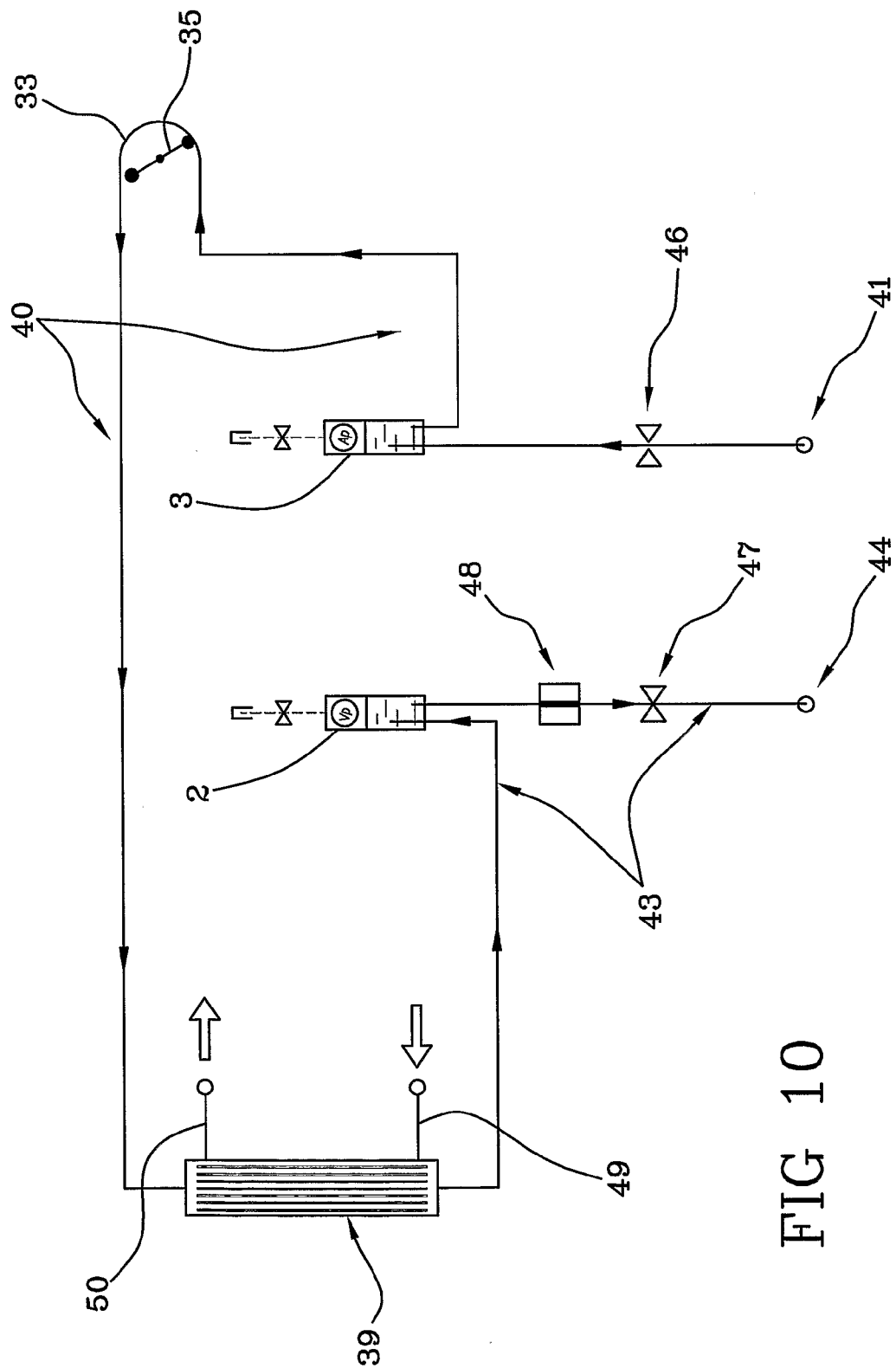
FIG. 10 is a dialysis apparatus which uses the dialysis set of FIG. 9.

FIG. 10 illustrates a blood treatment apparatus (in particular a dialysis apparatus) including the blood treatment device 39, which apparatus comprises a blood chamber, a dialysis liquid chamber and a semipermeable membrane that separates the blood chamber from the dialyser liquid chamber. The blood chamber is connected to a dialysis set for blood transport. In particular the dialysis set comprises a venous chamber provided with the filter of the present invention. The dialysis set of the apparatus of FIG. 10 can be that of FIG. 9. The dialysis apparatus comprises a control unit (not illustrated). The dialysis apparatus further comprises an arterial clamp 46 and a venous clamp 47 controlled by the control unit and located between the arterial chamber 3 and the patient arterial end 41 and, respectively, between the venous chamber 2 and the patient venous end 44. The dialysis apparatus comprises an air bubble detector 48 operating between the venous chamber 2 and the venous clamp 47. The dialysis apparatus further comprises a dialysis liquid circuit comprising a fresh dialyser liquid supply line 49, connected to an inlet of the dialysis liquid chamber of the blood treatment device 39, and a used dialysis liquid discharge line 50, connected to an outlet of the dialysis liquid chamber. The dialysis liquid circuit comprises other elements of any one of the dialysis liquid circuits of known type.

It has been observed that during the priming stage of the dialysis set (in which, as is known, air is expelled and the circuit rinsed by the priming fluid) there is only a small risk of air bubbles getting trapped internally of the tubular filter, especially at the top of the filter, below the head. It has also been noted that during the treatment the blood flows through the filtering surface of the filter with a regular flow and without excessive turbulence and formation of foam. It has also been seen that during the treatment stage the blood flows across the filtering surface of the filter with an improvement in the homogeneity of the blood velocity, i.e. the punctual velocity of the blood crossing the upper openings 13 is about equal to or nearly the same as the punctual velocity of the blood crossing the lower openings 14. Further, the filtering capacity of the filter, i.e. its ability to hold back any particles that are contained in the blood (for example blood clots or particles which detach from the membrane of the blood treatment device) and which must not reach the vascular access of the patient, is absolutely suitable for patient safety.

LEGEND

1 Cartridge for extracorporeal blood circuit
2 Venous blood chamber
3 Arterial blood chamber
4 Blood filter
5 Recipient of venous blood chamber 2
6 Top of recipient 5
7 Bottom of recipient 5
8 Lateral wall of recipient 5
9 Blood inlet to recipient 5
10 Blood outlet from recipient 5
11 Upper portion of the filtering wall of the filter 4
12 Lower portion of the filtering wall of the filter 4
13 Upper openings arranged in the upper portion 11
14 Lower openings arranged in the lower portion 12
15 Inclined and connected surface inferiorly delimiting each of the lower openings 14 which are smaller and closer to the outlet 10
16 Upper head of the filtering wall of the filter 4
17 Fluid passage openings arranged in the upper head 16
18 First ribs (longitudinal or axial)
19 Second ribs (circumferential or meridian)
20 Membrane device for detecting pressure in the venous blood chamber
21 First access port of the venous blood chamber 2 communicating with the blood inlet 9
22 Second access port of the venous blood chamber 2 communicating with the blood outlet 10
23 Conduit integrated in the cartridge connecting the first access port 21 to the blood inlet 9
24 Base of the filter 4
25 -
26 -
27 -
28 -
29 -
30 Membrane device for detecting pressure in the arterial blood chamber
31 First access port of the arterial blood chamber 3 (blood inlet port)
32 Second access port of the arterial blood chamber 3 (blood outlet port)
33 Pump tube
34 Second tubular extension coupled to the pump tube 33
35 Blood pump
36 Internal conduit integrated in the cartridge 1
37 Tubular connector
38 Tract of arterial line
39 Blood treatment device (dialyser/membrane separator)
40 Arterial line of the extracorporeal blood circuit
41 Patient end of the arterial line 40
42 Device end of the arterial line 40
43 Venous line of the extracorporeal blood circuit
44 Patient end of the venous line 43
45 Device end of the venous line 43
46 Arterial clamp
47 Venous clamp
48 Air bubble detector
49 Fresh dialysis liquid supply line
50 Used dialysis liquid discharge line

The invention claimed is:

1. A blood transfer chamber, comprising:
a recipient having a top, a bottom, a lateral wall, an inlet and an outlet; the lateral wall extending between the top and the bottom; the lateral wall having at least a first transversal section having a first area, the outlet being arranged on the bottom, the outlet having a second transversal section having a second area which is smaller than the first area; and
a filter arranged between the inlet and the outlet, the filter having a filtering wall comprising an upper portion and a lower portion, the upper portion having a plurality of upper openings, the lower portion having a plurality of lower openings;
wherein the upper openings and lower openings are configured in such a way that the upper portion offers a resistance to fluid passage per surface unit which is lower than a resistance to fluid passage per surface unit offered by the lower portion;
wherein the surface area of the upper openings per surface unit of the upper portion is greater than the surface area of the lower openings per surface unit of the lower portion.

2. The chamber of claim 1, wherein:
the upper portion has a first value which is defined by the surface of the upper openings per surface unit of the upper portion;
the lower portion has a second value which is defined by the surface of the lower openings per surface unit of the lower portion; and
the first value is greater than the second value.

3. A blood transfer chamber, comprising:
a recipient having a top, a bottom, a lateral wall, an inlet and an outlet; the lateral wall extending between the top and the bottom; the lateral wall having at least a first transversal section having a first area, the outlet being arranged on the bottom, the outlet having a second transversal section having a second area which is smaller than the first area; and
a filter arranged between the inlet and the outlet, the filter having a filtering wall comprising an upper portion and a lower portion, the upper portion having a plurality of upper openings, the lower portion having a plurality of lower openings;
wherein the upper openings and lower openings are configured in such a way that the upper portion offers a resistance to fluid passage per surface unit which is lower than a resistance to fluid passage per surface unit offered by the lower portion;
wherein the upper openings are on average larger than the lower openings.

4. The chamber of claim 1, wherein the filter is made of a single piece of a plastic material.

5. The chamber of claim 1, wherein the filtering wall is tubular, with a lower end thereof which is open or which is closed by a further filtering wall.

6. The chamber of claim 1, wherein the filter extends between the bottom and the top.

7. The chamber of claim 1, wherein the filter has a lower end having a base which is solidly fixed to the bottom about the outlet.

8. The chamber of claim 3, wherein the upper openings are all larger than the lower openings.

9. A blood transfer chamber, comprising:
a recipient having a top, a bottom, a lateral wall, an inlet and an outlet; the lateral wall extending between the top and the bottom; the lateral wall having at least a first transversal section having a first area, the outlet being arranged on the bottom, the outlet having a second transversal section having a second area which is smaller than the first area; and
a filter arranged between the inlet and the outlet, the filter having a filtering wall comprising an upper portion and a lower portion, the upper portion having a plurality of upper openings, the lower portion having a plurality of lower openings;
wherein the upper openings and lower openings are configured in such a way that the upper portion offers a resistance to fluid passage per surface unit which is lower than a resistance to fluid passage per surface unit offered by the lower portion;
wherein the size and/or the width, and/or the height of the upper openings and/or the lower openings in the filtering wall increases going from the bottom thereof towards the top thereof.

10. The chamber of claim 9, wherein the increase in size, and/or width, and/or height, is gradual.

11. The chamber of claim 9, wherein at least a part of the upper openings is from one and a half to six times larger than at least a part of the lower openings.

12. The chamber of claim 9, wherein the upper openings located highest or furthest from the outlet are at least twice as large as the lower openings which are positioned lowest, or closest to the outlet.

13. The chamber of claim 1, wherein the width of the upper openings and/or the lower openings is substantially constant.

14. The chamber of claim 1, wherein the upper openings and/or the lower openings arranged at a same distance from the outlet are the same size.

15. The chamber of claim 1, wherein some of the upper openings and/or the lower openings are on average further from the outlet and are also bigger with respect to others of the upper openings and/or the lower openings.

16. The chamber of claim 1, wherein the lower openings arranged lowest are smaller than all or a majority of the other openings in the filter.

17. The chamber of claim 16, wherein the smallest lower openings are arranged in an annular fashion about a longitudinal axis of the filtering wall.

18. The chamber of claim 16, wherein each of the smallest of the lower openings is inferiorly delimited by an inclined surface, the inclination extending in a downwards direction proceeding from outside towards inside of the tubular filtering wall.

19. The chamber of claim 18, wherein all or a majority of the remaining lower openings and/or upper openings are each inferiorly delimited by an inclined surface which is curved outwards, the inclination extending in a downwards direction proceeding from an inside towards an outside of the tubular filtering wall.

20. The chamber of claim 1, wherein the filtering wall is essentially cylindrical or truncoconical.

21. The chamber of claim 1, wherein the filtering wall is superiorly provided with a head which is closed or which exhibits a further plurality of openings for fluid passage.

22. The chamber of claim 1, wherein the filtering wall comprises a plurality of first ribs and a plurality of second ribs, the first ribs extending in an axial direction, the second ribs extending in a circumferential direction, the first ribs intersecting with the second ribs, the first ribs being reciprocally aligned and distanced in a circumferential direction, each first rib being at a same circumferential distance from two adjacent first ribs, the second ribs being reciprocally coaxial and distanced in an axial direction, each second rib being more distant in an axial direction from an immediately-above second rib than from an immediately-below second rib.

23. The chamber of claim 22, wherein the second ribs are arranged more externally than the first ribs.

24. The chamber of claim 1, wherein the upper openings define a passage section per surface unit of the filtering wall which is comprised between 0.25 and 0.65.

25. The chamber of claim 1, wherein the lower openings define a passage section per surface unit of the filtering wall which is comprised between 0.15 and 0.55.

26. The chamber of claim 1, wherein the filtering wall is essentially cylindrical or truncoconical, and wherein the upper openings and/or the lower openings extend parallel to a generatrix of the filtering wall.

27. The chamber of claim 1, wherein the inlet is arranged closer to the top than to the outlet.

28. The chamber of claim 1, wherein a top end of the filter is arranged closer to the outlet than to the inlet.

29. The chamber of claim 1, wherein the inlet is arranged higher than a top end of the filter.

30. The chamber of claim 1, wherein the lower openings and/or the upper openings are arranged in an annular fashion about a longitudinal axis of the filtering wall.

31. The chamber of claim 1, wherein the lower openings and/or the upper openings define overall a total passage section which is greater than the second transversal section area.

32. The chamber of claim 31, wherein the total passage section is from five to ten times greater than the second transversal section area.

33. An extracorporeal blood transport line, comprising at least a patient end which is configured for connection with a vascular access, and at least a device end which is configured for connection with a blood treatment device, wherein it comprises a blood transfer chamber realised according to claim 1.

34. An extracorporeal blood transport set comprising a venous blood line and an arterial blood line, which venous blood line is provided with a venous blood chamber, the arterial blood line being provided with a pump tube; wherein the venous blood line is realised as in claim 33.

35. An extracorporeal blood treatment apparatus comprising: an extracorporeal blood treatment device having a first chamber, a second chamber and a semipermeable membrane which separates the first chamber from the second chamber; an extracorporeal blood transport set connected to the first chamber; and a treatment fluid transport circuit connected to the dialysis liquid chamber; wherein the extracorporeal blood transport set of the apparatus is realised as in claim 34.

36. A blood transfer chamber, comprising:
a recipient having a top, a bottom, a lateral wall, an inlet and an outlet; the lateral wall extending between the top and the bottom; the lateral wall having at least a first transversal section having a first area, the outlet being arranged on the bottom, the outlet having a second transversal section having a second area which is smaller than the first area; and a filter arranged between the inlet and the outlet, the filter having a filtering wall comprising an upper portion and a lower portion, the upper portion having a plurality of upper openings, the lower portion having a plurality of lower openings;

wherein the upper openings and lower openings are configured in such a way that the upper portion offers a resistance to fluid passage per surface unit which is lower than a resistance to fluid passage per surface unit offered by the lower portion;

wherein the size of the openings in the filtering wall increases going from the bottom thereof towards the top thereof.

37. The chamber of claim 36, wherein the size of the openings in the filtering wall increases gradually going from the bottom thereof towards the top thereof.

38. The chamber of claim 1, wherein the upper openings are distributed more closely than the lower openings.

\* \* \* \* \*

UNITED STATES PATENT AND TRADEMARK OFFICE
CERTIFICATE OF CORRECTION

PATENT NO. : 8,641,657 B2  Page 1 of 1
APPLICATION NO. : 12/517020
DATED : February 4, 2014
INVENTOR(S) : Ribolzi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 839 days.

Signed and Sealed this
Twenty-second Day of September, 2015

Michelle K. Lee
*Director of the United States Patent and Trademark Office*